United States Patent [19] [11] 3,974,104
Foster et al. [45] Aug. 10, 1976

[54] DENTURE BASES OF X-RAY OPAQUE POLYMERS

[75] Inventors: John Foster, Sheerness; Vallabhbhai Bhanabhai Ahir, London, both of England

[73] Assignee: The Amalgamated Dental Company Limited, London, England

[22] Filed: Mar. 14, 1973

[21] Appl. No.: 340,941

[30] Foreign Application Priority Data
Mar. 15, 1972 United Kingdom............... 12135/72

[52] U.S. Cl................................... 252/478; 32/2; 106/35; 526/89; 526/328; 526/348
[51] Int. Cl.² ........................................ C09K 3/00
[58] Field of Search ............ 32/2; 106/35; 252/478; 260/80 L

[56] References Cited
UNITED STATES PATENTS

| | | | |
|---|---|---|---|
| 2,439,374 | 4/1948 | Leader et al......................... | 252/478 |
| 3,012,018 | 12/1961 | Marinelli et al.................... | 260/80 L |
| 3,016,369 | 1/1962 | Montermoso et al............ | 260/80 L |
| 3,536,688 | 10/1970 | Aufdermarsh, Jr. .............. | 260/80 L |
| 3,715,331 | 2/1973 | Molnar .......................... | 252/478 X |

Primary Examiner—Leland A. Sebastian

[57] ABSTRACT

A radio opaque denture base formed of a copolymer of an ethylenically unsaturated monomer containing chemically bound tin together with at least one ethylenically unsaturated monomer, the ethylenically unsaturated monomer containing chemically bound tin being an ester of trialkyl tin and an ethylenically unsaturated acid such as tributyl tin ethacrylate. In a preferred embodiment the copolymer is a novel copolymer derived from two ethylenically unsaturated tin containing monomers one of which is trimethyl tin methacrylate and the other is a trialkyl tin methacrylate other than trimethyl tin methacrylate. In another preferred embodiment the copolymer is a novel copolymer derived from an ester of trialkyl tin and an ethylenically unsaturated carboxylic acid together with two or more other ethylenically unsaturated monomers, one of which is a long chain alkyl acrylate or methacrylate and another of which is a lower alkyl acrylate or methacrylate.

15 Claims, No Drawings

DENTURE BASES OF X-RAY OPAQUE POLYMERS

This invention is concerned with improvements in and relating to denture bases formed from radiopaque polymeric materials and polymeric materials suitable for the manufacture of such denture bases.

Currently, the great majority of denture bases are made from acrylic resins, especially polymers of methyl methacrylate, and such denture bases suffer from one marked disadvantage in that they are radiolucent, i.e. they are essentially translucent to X-rays. This radiolucency is a disadvantage since it makes it very difficult to locate the denture base or a part thereof in the body if it is accidentally swallowed or inhaled as a result of an accident. In the event of such an accident it is clearly desirable that the denture base or any fragment thereof be located but this is extremely difficult in the case of radiolucent materials and there is, accordingly, a need for denture bases made of radiopaque material.

It has now been found, in accordance with the present invention, that certain polymers containing ethylenically bound tin possess interesting radiopaque properties and, at the same time, are aethsetically attractive in that they are generally clear translucent polymers.

Broadly, therefore, in accordance with one aspect of the invention, there is provided a denture base formed of a copolymer of an ethylenically unsaturated monomer containing chemically bound tin together with one or more other ethylenically unsaturated monomers; the ethylenically unsaturated monomer containing chemically bound tin being an ester of trialkyl tin and an ethylenically unsaturated acid, especially acrylic acid, or preferably, methacrylic acid.

Thus the preferred ethylenically unsaturated monomers containing chemically bound tin may be represented by the formula:

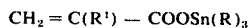

$$CH_2 = C(R^1) - COOSn(R)_3$$

in which R is a lower alkyl group, for example containing from 1 to 6 carbon atoms, and $R^1$ is a hydrogen atom or a methyl group. A readily available trialkyl tin acrylate of the above formula is tributyl tin methacrylate and, hence, this will usually be used as tin-containing monomer. However, in accordance with another embodiment of the invention, it has been found that better results, insofar as polymer strength and elasticity are concerned, may be obtained by using a mixture of two tin-containing monomers, one of which is trimethyl tin methacrylate and the other of which is another trialkyl tin methacrylate, especially tributyl tin methacrylate.

Accordingly, in accordance with another embodiment thereof, the invention provides a tin-containing polymer which is a copolymer of trimethyl tin methacrylate, a trialkyl tin methacrylat (other than trimethyl tin methacrylate) and one or more other ethylenically unsaturated monomers.

The tin-containing monomer(s) are conveniently used in such amounts as to provide from 2.5 to 10% by weight, preferably about 5% by weight, of tin in the polymer. Where two tin-containing monomers are employed, the trimethyl tin methacrylate preferably forms a minor proportion, by weight, of the total weight of the tin-containing monomers, for example from 30–45% by weight, preferably about 40% by weight of the total weight of tin-containing monomers.

The other monomer(s) from which the tin-containing copolymer is derived, will suitably comprise a major proportion by weight of a lower alkyl acrylate or, preferably, a lower alkyl methacrylate, especially methyl methacrylate. The copolymer may also contain minor amounts e.g. up to 10% by weight, of other ethylenically unsaturated monomers and, particularly, may contain poly-unsaturated cross-linking monomers such as the diacrylates or dimethacrylates of dihydric alcohols, for example diethylene glycol dimethacrylate. It has further been found, in accordance with another feature of the invention, that the use of a long chain alkyl acrylate or methacrylate as one of the comonomers from which the copolymer is derived, leads to an improved polymer having improved impact resistance.

Thus, in accordance with a further feature of the invention, there is provided a polymer derived from an ester of trialkyl tin and an ethylenically unsaturated carboxylic acid (preferably a trialkyl tin acrylate or methacrylate or mixture thereof) together with two or more other ethylenically unsaturated monomers, one of which is a long chain alkyl acrylate or methacrylate (containing for example, from 8 to 20 carbon atoms in the alkyl group) and another of which is a lower alkyl acrylate or methacrylate, for example methyl acrylate. The long chain alkyl acrylate or methacrylate suitably forms from 5 to 15% by weight of the polymer, preferably about 8% thereof.

The tin-containing copolymer is conveniently prepared by polymerising the monomers in the presence of a free radical catalyst, for example a peroxide catalyst such as benzoyl peroxide. When the polymer is required in finely divided form (for example for the preparation of a denture base as described below), the polymerization is suitably carried out as a suspension polymerization by polymerizing the monomers in water with stirring in the presence of a suspending agent such as starch, an ethylene/maleic anhydride copolymer or polyethylene oxide.

The denture base in accordance with the invention is suitably prepared from a dough prepared by mixing finely divided, e.g. having a particle size of less than 60 mesh, preformed tin-containing copolymer with one or more liquid ethylenically unsaturated monomers. The tin-containing copolymer may be any one of those described above and the liquid monomer is preferably an alkyl acrylate. In accordance with a further feature of the invention, the liquid monomer component preferably comprises a mixture of a lower alkyl acrylate or methacrylate and a minor proportion of a long chain alkyl acrylate or methacrylate, the latter suitably being used in amounts so as to form about 5 to 15% by weight, preferably about 8% by weight, of the final product. The resultant dough, the flow characteristics of which are improved by employing a long chain alkyl acrylate or methacrylate as a part of the liquid monomer component, is then forced into the dental flask and cured therein, for example by the action of heat or a chemical initiator, e.g. a peroxide catalyst such as benzoyl peroxide.

The invention also provides a two-part pack for preparing the dough described above comprising one pack containing finely divided tin-containing copolymer and the other pack containing free liquid monomer(s).

In addition to their use as denture base materials, the copolymers described above (especially those derived from two tin-containing monomers and/or a mixture of a lower alkyl acrylate or methacrylate and a long chain acrylate or methacrylate), may also be used in other dental and medical applications wherein radiopacity is a desirable characteristic. Thus, the copolymers may be used to form artificial teeth or may be used as radiopaque medical cements.

In any event, however, the clarity and translucency of the copolymers greatly enhance their aesthetic appeal and they may, of course, be coloured with suitable pigments or dyestuffs where so desired.

In order that the invention may be well understood, the following Example is given by way of illustration only.

EXAMPLE a. 600 Grams of methylmethacrylate, 120 grams of tributyl tin methacrylate, 80 grams of trimethyl tin methacrylate and 8 grams of benzoyl peroxide are mixed together to form a homogeneous solution. This solution is then added to a solution of 64 grams of Polyox and 7.0 grams of ammonium phosphate in 1600 ml of water contained in a suitable polymerization vessel. The reaction mixture is then vigorously stirred and maintained at 80°C, under an atmosphere of nitrogen, for 1 hour until polymerization is complete.

The particulate tin-containing methyl methacrylate/tributyl tin methacrylate/trimethyl tin methacrylate copolymer so obtained is filtered off from the reaction mixture, washed with water and then dried at 70°C. Finally, the polymer is sieved through a 60 mesh sieve. The polymer powder so obtained has a residual benzyl peroxide content of 0.7% at a specific viscosity of 2.04 as measured as a 1% chloroform solution at 25°C.

b. 23.5 Grams of the powdered polymer from (a) above are blended with 10 ml of a liquid comprising 5% lauryl methacrylate, 8% ethylene glycol dimethacrylate and 87% methyl methacrylate. The blended mixture acquires a dough-like consistency after about 10 minutes and has a working time of about 10 minutes at ambient temperature of 21°C.

The resultant dough is cured in a plaster mould contained in a metal flask using the following curing cycle. Firstly, the clamped flask is immersed in a boiling water bath from which the heat supply has been cut off, for 20 minutes, whilst ensuring that there is ample water well covering the flask. The heat supply to the water bath is then reconnected at a low rate to hold the temperature for a further 20 minutes. The heat is then increased until the water boils and boiling is continued for a further 20 minutes. The flask is then removed and allowed to cool, preferably slowly.

Alternatively, the dough may be polymerised by dry heating in the flask for 8 hours at 80°C.

In both cases the physical properties of the cured materials comply with the requirements of international specifications, e.g. ADA or DSI specifications for heat cured denture base materials. The radiopacity of these materials is equivalent to an acrylic polymer containing 20% by weight of barium sulphate as radiopacifying agent.

We claim:

1. A denture base formed of a copolymer of an ethylenically unsaturated monomer containing chemically bound tin together with at least one ethylenically unsaturated monomer which does not contain tin, the ethylenically unsaturated monomer containing chemically bound tin being an ester of trialkyl tin and an ethylenically unsaturated acid and the non-tin containing monomer comprising a major proportion by weight of a lower alkyl acrylate or lower alkyl methacrylate.

2. A denture base according to claim 1 in which the ethylenically unsaturated acid is acrylic acid or methacrylic acid.

3. A denture base according to claim 2 in which the ethylenically unsaturated monomer containing chemically bound tin has the formula:

$$CH_2 = C(R^1) - COOSn(R)_3$$

in which R is a lower alkyl group containing from 1 to 6 carbon atoms and $R^1$ is a hydrogen atom or methyl group.

4. A denture base according to claim 1 in which the ethylenically unsaturated monomer containing chemically bound tin is tributyl tin methacrylate.

5. A denture base according to claim 1 in which the copolymer is derived from two different ethylenically unsaturated tin-containing monomers one of which is trimethyl tin methacrylate and the other is a second trialkyl tin methacrylate.

6. A denture base according to claim 5 in which the trimethyl tin methacrylate forms from 30 to 45 percent by weight of the tin-containing monomers.

7. A denture base according to claim 1 in which the copolymer contains from 2.5 to 10 percent by weight of tin.

8. A denture base according to claim 1 in which the non-tin containing monomers comprise a minor proportion by weight of a polyethylenically unsaturated cross-linking monomer.

9. A denture base according to claim 1 in which the copolymer includes the moiety of a long chain alkyl acrylate or methacrylate monomer.

10. A denture base according to claim 1 in which the copolymer includes the moiety of an ester of trialkyl tin and an ethylenically unsaturated carboxylic acid together with two or more other ethylenically unsaturated monomers, one of which is a long chain alkyl acrylate or methacrylate and another of which is a lower alkyl acrylate or methacrylate.

11. A denture base according to claim 10 in which the long chain acrylate contains from 8 to 20 carbon atoms.

12. A denture base according to claim 10 in which the copolymer includes the moieties of a mixture containing from 5 to 15 percent by weight of the long chain alkyl acrylate or methacrylate.

13. A process for preparing a denture base which comprises mixing a finely divided tin-containing copolymer which is a copolymer of an ethylenically unsaturated monomer containing chemically bound tin, said monomer containing chemically bound tin being an ester of trialkyl tin and an ethylenically unsaturated acid and at least one other ethylenically unsaturated non-tin containing monomer; said non-tin containing monomer comprising a major proportion by weight of a lower alkyl acrylate or lower alkyl methacrylate, with one or more liquid alkyl acrylate or methacrylates to form a dough, placing the resultant dough into a dental flask and then curing the dough in the dental flask.

14. A tin-containing polymer which is a copolymer of trimethyl tin methacrylate, a trialkyl tin methacrylate having more than one carbon atom in the alkyl group, and at least one other ethylenically unsaturated monomer.

15. A copolymer derived from an ester of trialkyl tin and an ethylenically unsaturated carboxylic acid together with at least two other ethylenically unsaturated monomers, one of said other ethylenically unsaturated monomers being a long chain alkyl or methacrylate and another of which is a lower alkyl acrylate or methacrylate.

* * * * *